(12) United States Patent
Cerello et al.

(10) Patent No.: US 10,197,688 B2
(45) Date of Patent: Feb. 5, 2019

(54) PHANTOM AND METHOD FOR VERIFYING THE CALIBRATION OF PET SCANNERS

(71) Applicant: DIXIT S.R.L., Turin (IT)

(72) Inventors: Piergiorgio Cerello, Turin (IT); Stephane Chauvie, Turin (IT); Andrea Gallamini, Turin (IT); Alexandru Mihail Cristian Stancu, Turin (IT)

(73) Assignee: Dixit S.R.L., Turin (IT)

( * ) Notice: Subject to any disclaimer, the term of this patent is extended or adjusted under 35 U.S.C. 154(b) by 940 days.

(21) Appl. No.: 14/417,289

(22) PCT Filed: Aug. 9, 2013

(86) PCT No.: PCT/IB2013/056514
§ 371 (c)(1),
(2) Date: Jan. 26, 2015

(87) PCT Pub. No.: WO2014/024167
PCT Pub. Date: Feb. 13, 2014

(65) Prior Publication Data
US 2015/0212219 A1    Jul. 30, 2015

(30) Foreign Application Priority Data
Aug. 10, 2012    (IT) .............................. TO2012A0721

(51) Int. Cl.
*G01T 7/00*     (2006.01)
*A61B 6/00*     (2006.01)
*A61B 6/03*     (2006.01)

(52) U.S. Cl.
CPC .............. *G01T 7/005* (2013.01); *A61B 6/037* (2013.01); *A61B 6/583* (2013.01); *G06T 2207/10104* (2013.01)

(58) Field of Classification Search
CPC ... G01T 1/2985; G01T 1/1642; G01T 1/1644; G01T 1/202; G01T 1/172
See application file for complete search history.

(56) References Cited

U.S. PATENT DOCUMENTS

| 2009/0127451 A1* | 5/2009 | Watson ................. A61B 6/583 250/252.1 |
| 2009/0283668 A1* | 11/2009 | Gilbertson ............. A61B 6/037 250/363.03 |
| 2010/0198063 A1* | 8/2010 | Huber ...................... A61B 5/05 600/437 |

OTHER PUBLICATIONS

Doot et al. "Instrumentation factors affecting variance and bias of quantifying tracer uptake with PET/CT" Med. Phys. 37 (11) Nov. 2010, pp. 6035-6046.*

(Continued)

*Primary Examiner* — David Porta
*Assistant Examiner* — Mamadou Faye
(74) *Attorney, Agent, or Firm* — Abel Law Group, LLP

(57) ABSTRACT

Phantom for verifying the calibration of PET scanners, comprising a substantially cylindrical body having a cross section with a convex curvilinear profile, and a plurality of spheres placed within said body, comprising a solid matrix of germanium-68, the phantom being characterized in that it further comprises a reference sphere filled with a solid matrix of germanium-68, said reference sphere being connected to the phantom in such a way that it can be removed and replaced in the same position.

19 Claims, 4 Drawing Sheets

(56) References Cited

OTHER PUBLICATIONS

Doot, R. K., Scheuermann, J. S., Christian, P. E., Karp, J. S., & Kinahan, P. E. (2010). Instrumentation factors affecting variance and bias of quantifying tracer uptake with PET/CT. Medical physics, vol. 37, No. 11, 6035-6046. XP012144772.

Schwartz, J., Humm, J. L., Gonen, M., Kalaigian, H., Schoder, H., Larson, S. M., & Nehmeh, S. A. (2011). Repeatability of SUV measurements in serial PET. Medical physics, vol. 38, No. 5, 2629-2638. XP012145265.

Data Spectrum: "NEMA IEC Body Phantom SetTM", 2013, XP002715955, http://www.spect.com/pub/NEMA_IEC_Body_Phantom_Set.pdf.

International Search Report dated Nov. 22, 2013 for PCT/IB2013/056514.

\* cited by examiner

PHANTOM AND METHOD FOR VERIFYING THE CALIBRATION OF PET SCANNERS

The present invention relates to a phantom and a method for verifying the calibration of PET (Positron Emission Tomography) scanners.

Clinical trials play an essential part in modern medicine, because each new therapeutic procedure must undergo a process of evaluation of its efficacy and tolerance by patients before it is made available to the public. It is increasingly common for trial protocols to require the use of medical imaging technology.

Fludeoxyglucose positron emission tomography (FDG-PET) is a specific non-invasive diagnostic investigation method based on the acquisition of images of a patient's body by means of a suitable apparatus (a PET scanner), in order to study the metabolic processes of the tissue. This investigation method has excellent diagnostic accuracy and is used, in particular, in oncology, for the staging, restaging and follow-up of numerous cancer pathologies.

PET images can be used to describe the position and evaluate the intensity of metabolic processes within the tissues.

FDG-PET is therefore capable of detecting the persistence of living cancer cells at the time of diagnosis, during treatment and in case of recurrence of the cancer, with an overall accuracy greater than that of the conventional radiological imaging techniques such as computerized tomography (CT) or magnetic resonance (MR).

In particular, when the longitudinal changes in the activity of fludeoxyglucose in the tumour are visualized earlier during the therapy, it becomes possible to predict the clinical outcome earlier than with the standard anatomical measurements, and to modify the treatment if necessary.

The intensity of the metabolic activity can be measured with the PET scanner using an index called the SUV (Standardized Uptake Value).

The SUV is defined by the following expression:

$$SUV = \frac{[A_{PET}] \cdot \text{bodyweight}}{(A_{inj} \cdot \exp(\Delta t_{res}/\tau - A_{res}) \cdot \exp(\Delta t_{upt}/\tau)} \quad (1)$$

where $A_{PET}$ is the concentration of radioactivity in the tissues at the time t of acquisition of the PET images (expressed in MBq/Kg), and is measured directly in a known way by the PET scanner;

$A_{inj}$ is the dose of radiopharmaceutical (expressed in MBq) injected into the patient and measured at the moment of injection by means of an activity calibrator of a known type;

$A_{res}$ is the residual activity (expressed in MBq) which remains in the syringe after the injection of the patient, and is measured by means of an activity calibrator of a known type, $A_{res}$ being measured at the time t after the injection of the patient;

$t_{upt}$ is the time elapsing between the injection of the patient and the acquisition of the PET image;

$\tau$ is the decay constant of the radioisotope administered to the patient and used for carrying out the PET, and is determined analytically;

bodyweight is the patient's weight expressed in kg, and is measured with a personal weighing scale of a known type.

All the times are measured with standard clocks.

In order to be able to use the SUV as a semi-quantitative parameter and to compare SUVs obtained from the same patient at different moments (longitudinal analysis) or among different patients (cross-sectional analysis), the first step is that of calibrating all the measuring instruments used to measure the quantities shown in the above formula and associating an error with these instruments.

The procedures for calibrating the clocks, the personal weighing scales and the activity calibrator are known, and are based essentially on the measurement, with each instrument to be calibrated, of the respective parameters of reference objects for which these parameters are known in advance because they have previously been determined by corresponding universal calibration authorities.

On the other hand, the procedures for verifying the calibration of PET scanners are much more complicated and are time-consuming both in the step of data acquisition and in the step of analysing these data.

These procedures require the intervention of a skilled operator, and this often leads to errors and/or inaccuracies.

In particular, the operator has to handle radioactive substances in an unsealed condition in order to carry out these calibrations, and this obviously gives rise to problems regarding the radiation protection of the operator. This is because the known phantoms used for verifying the calibration of PET scanners require the operator to conveniently insert the radioactive substances into them to carry out the calibration of a PET scanner.

The object of the invention is therefore to propose a phantom and a method for verifying the calibration of PET scanners which enable the calibration to be performed in a simple, fast and efficient way, without being dependent on the manual intervention of the operator and without exposing the operator to risks of contamination.

This and other objects are achieved with a phantom for verifying the calibration of PET scanners whose characteristics are defined in Claim 1, and with a method for verifying the calibration of PET scanners as defined in Claim 10.

Specific embodiments are described in the dependent claims, the content of which is to be considered as an integral and essential part of the present description.

Further characteristics and advantages of the invention will be made clear by the following detailed description, provided purely by way of non-limiting example, with reference to the appended drawings, in which.

Briefly, the phantom of the present invention comprises a body having a known shape, defined according to international standards, and sealed radioactive sources, located within the phantom, consisting of a non-removable germanium gel.

The phantom of the present invention is used to apply the method of verifying the calibration of PET scanners described below.

After the calibration of the PET scanner has been verified, it can be used to carry out PET analyses on patients.

In order to carry out these analyses, it is necessary to know the weight (in kg) of the patients in order to use formula (1) to calculate the SUV. It is convenient, therefore, if the weight is determined with a personal weighing scale which is calibrated in accordance with the weight of the phantom used to verify the calibration of the PET scanner, in order to avoid dissimilarities in the parameters to be entered into equation (1).

In order to allow uniformity between the operations of verifying the calibration of the PET scanner and the subsequent operations of PET analysis of patients, another object of the invention is a kit for PET analysis, comprising a phantom as defined above and as described in detail below, a calibrated clock (for measuring the times to be entered into equation (1) for calculating the patient's SUV) and an object of known weight (to be used for calibrating the personal weighing scale for determining the patient's weight for the calculation of the patient's SUV). Alternatively, the object of known weight is not present, and the phantom, whose weight is known in advance, is used directly.

Figure 1:
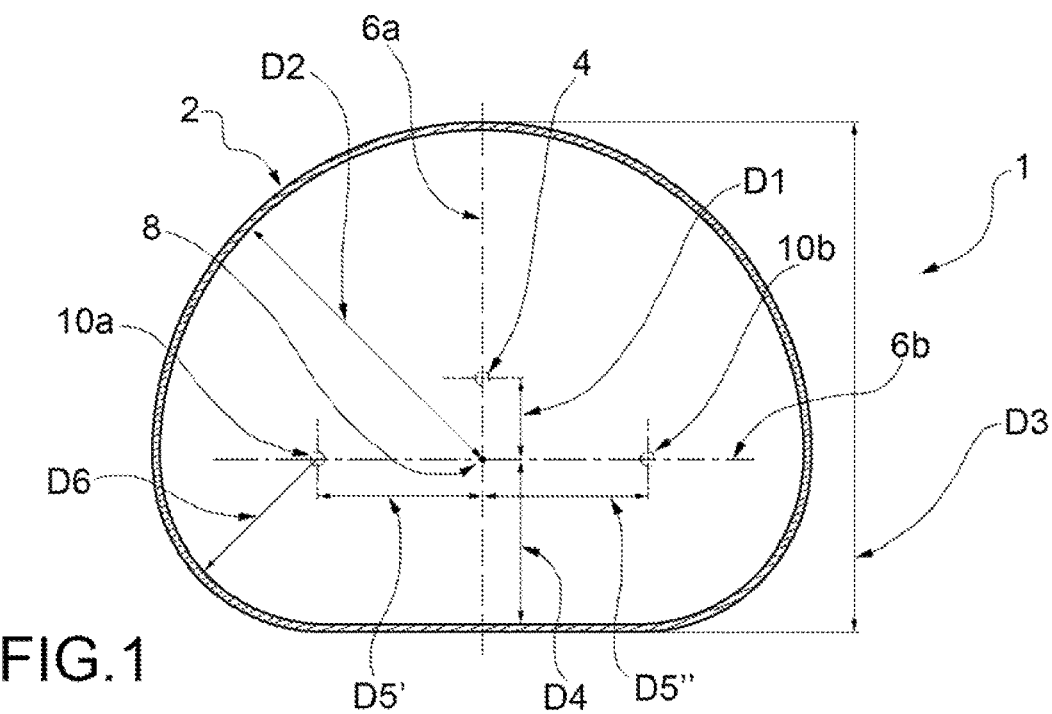
FIG. 1 is a complete cross-sectional view of a phantom according to the present invention.

In FIG. 1, the number 1 indicates the complete cross section of a phantom according to the present invention.

The phantom is preferably made of Plexiglas, particularly polymethyl methacrylate, and comprises a substantially cylindrical body 2 which advantageously has a height of at least 180 mm, a cross section 1 with a convex curvilinear profile, and a volume of 9.7 L. The wall defining the body 2 is, for example, 3 mm thick.

Within the body 2, a centre 4 is identified, and a first transverse axis 6a and a second transverse axis 6b, perpendicular to the first axis 6a, are defined. The centre 4 is located on the first transverse axis 6a and is spaced apart from the second transverse axis 6b by a predetermined distance D1, equal to 35 mm for example.

The first transverse axis 6a and the second transverse axis 6b intersect each other at an intersection point 8.

The body 2 of the phantom has a predetermined internal dimension D2, defined as the distance between the intersection point 8 and the upper inner wall of the body 2 (where the term "upper" refers to the arrangement of the cross section 1 as shown in FIG. 1) along a diagonal direction, which is preferably equal to 147 mm.

The body 2 has a predetermined external dimension D3, which is defined as the length of the first transverse axis 6a plus the thickness of the wall of the body 2, and which is preferably equal to 230 mm.

The second transverse axis 6b is spaced apart from the lower inner wall of the body 2 by a predetermined distance D4, equal to 77 mm for example.

On the second transverse axis 6b there are defined two foci 10a and 10b which are spaced apart from the first transverse axis 6a by predetermined distances D5' and D5" respectively, equal to 70 mm for example.

The two foci 10a and 10b are respectively spaced apart from the lower inner wall of the body 2 along a diagonal direction by a predetermined distance D6, equal to 77 mm for example.

Figure 2:
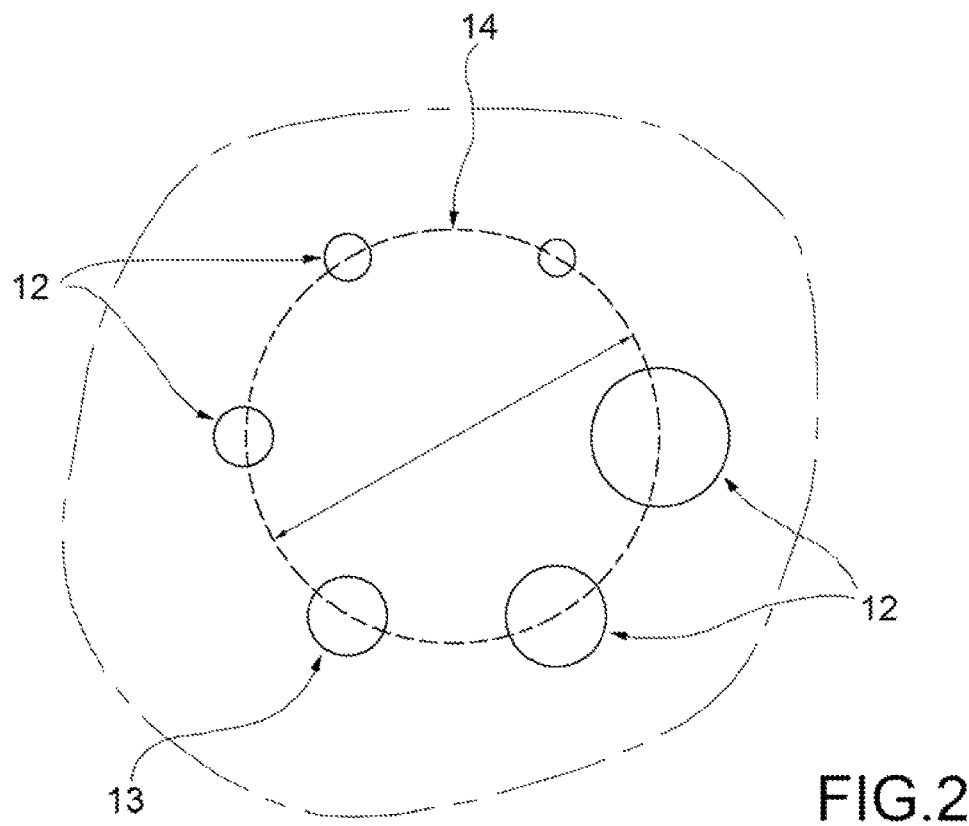
FIG. 2 is a cross-sectional view of a detail of the phantom of FIG. 1.

FIG. 2 shows a cross-sectional view of a detail of the phantom of FIG. 1.

The phantom comprises, within the body 2, a plurality of fillable spheres 12, these spheres being five in number for example, and preferably having respective inside diameters of 10 mm, 13 mm, 17 mm, 28 mm and 37 mm, and a wall thickness less than or equal to 1 mm. Advantageously, the spheres are placed along a circumference 14 having a predetermined diameter, equal to 114.4 mm for example.

The spheres 12 are preferably made of polymethyl methacrylate or glass or other plastic material.

The phantom further comprises a reference sphere 13 preferably having an inside diameter of 22 mm, connected to the phantom in a known way so that it can easily be removed and replaced in the same starting position, for use as a reference source in a common activity calibrator.

Figure 3:
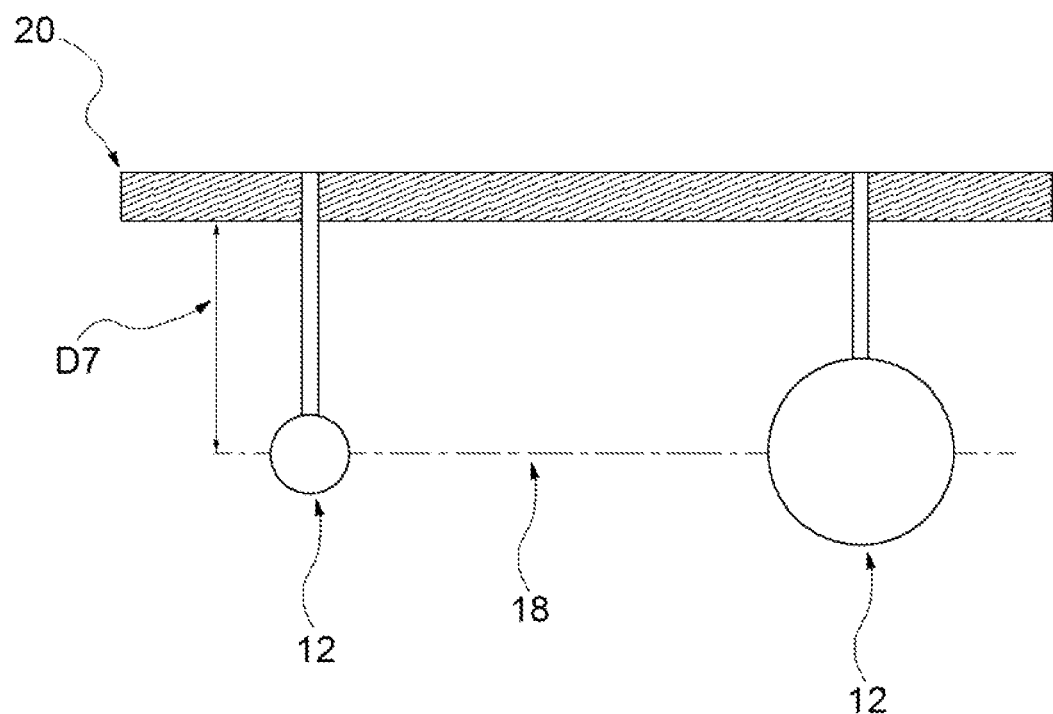
FIG. 3 is a view in longitudinal section of a central portion of the phantom according to the present invention.

FIG. 3 shows a view in longitudinal section of a central portion of the phantom according to the present invention, in which two of the spheres 12 are shown.

The spheres 12 are inserted into the phantom by opening a mounting plate 20 placed in correspondence of the upper surface.

The centres of the spheres 12 are aligned along a third transverse axis 18 placed at a predetermined distance D7, equal to 70 mm for example, from the mounting plate 20, in such a way that the spheres are axially located on the same transverse line.

The transverse positioning of the spheres must be such that the centres of the spheres are positioned at a predetermined distance, for example 5.72 cm, from the centre 4 of the phantom.

Figure 4:
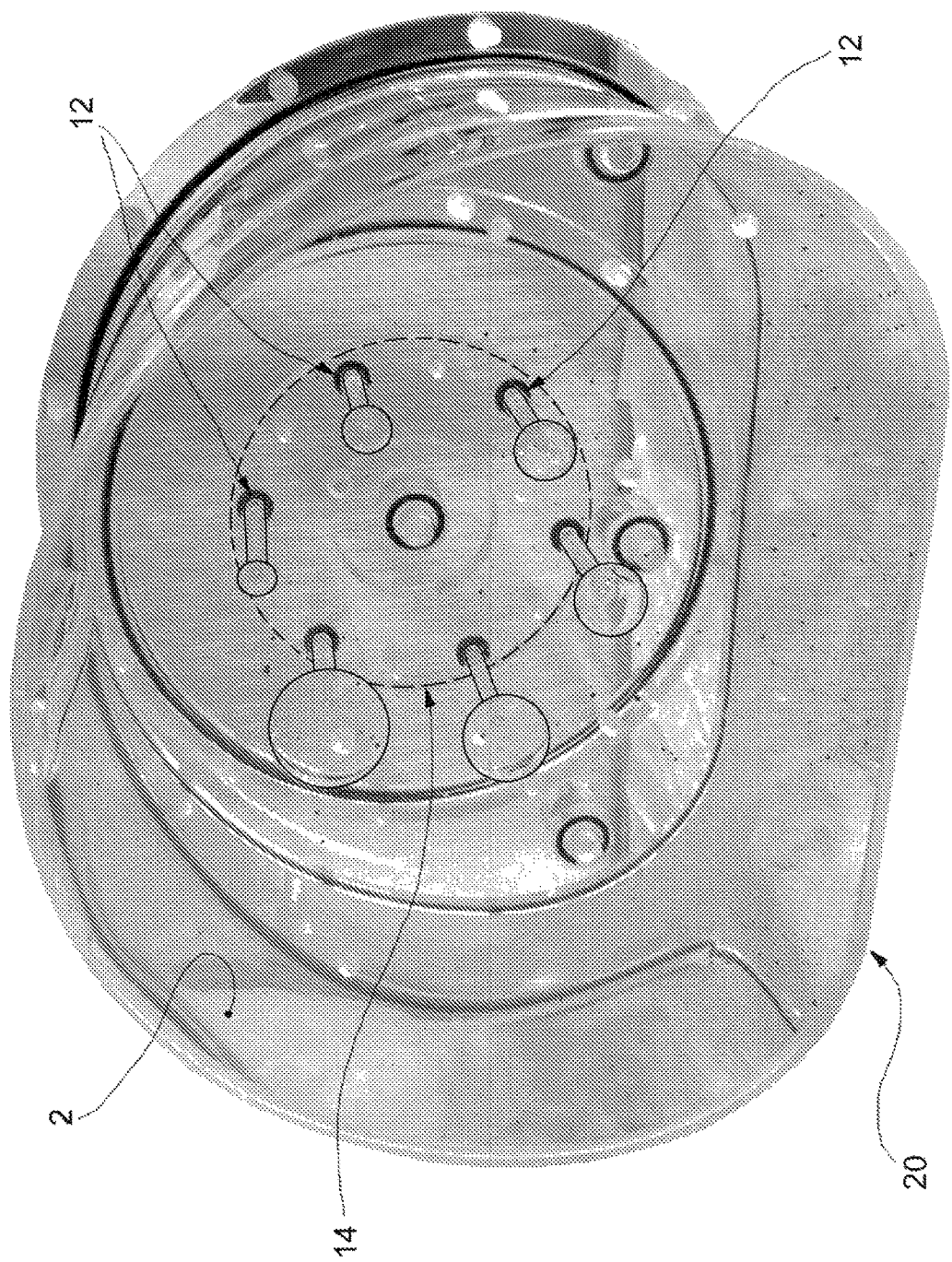
FIG. 4 is a three-dimensional perspective view of the phantom of the present invention.
Figure 5:
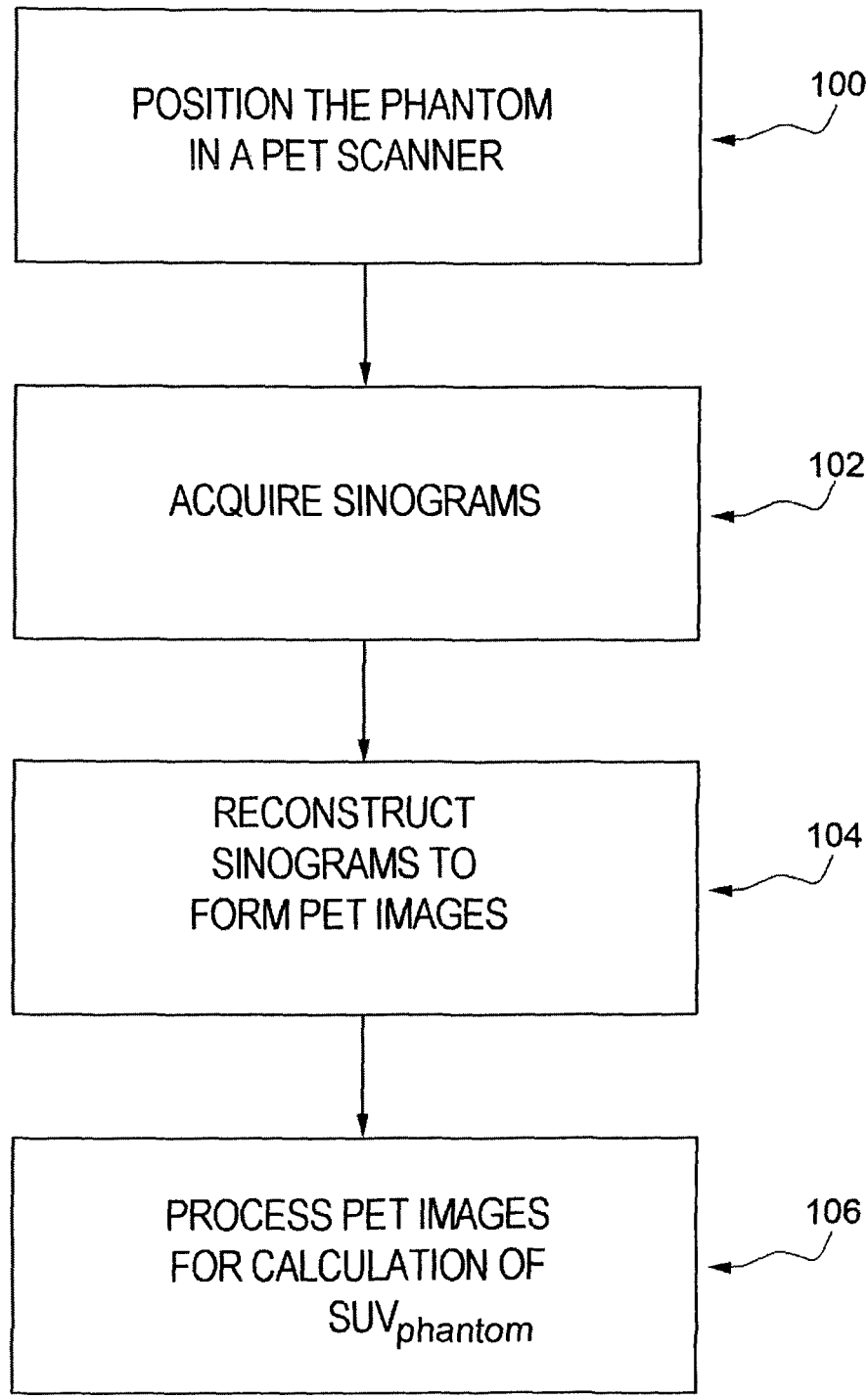
FIG. 5 is a block diagram of the steps of the method of verifying the calibration of PET scanners according to the present invention.

FIG. 4 is a three-dimensional perspective view of the phantom of the present invention, in which the elements already described with reference to the preceding figures are indicated by the same reference numbers.

The body 2 of the phantom is filled with a solid matrix of germanium-68.

In particular, the spheres 12 are filled with a solid matrix of germanium-68 having an activity concentration $A_{spheres}$ of the solid matrix of germanium-68 four times greater than the area of the body 2 surrounding said spheres 12, varying from 42.4 kBq/ml to 10.6 kBq/ml with a variability of 3%. The activity concentration range $A_{phantom}$ of the area surrounding the spheres 12 may vary from 10.6 kBq/ml to 2.65 kBq/ml with a variability of 3%.

Alternatively, the spheres 12 are not filled with a solid matrix of germanium-68 as described above, but are themselves made of said solid matrix of germanium-68.

The reference sphere 13 is filled with an activity concentration equal to that of the spheres 12, and the activity concentration range $A_{reference\_sphere}$ of this reference sphere 13 can vary from 42.4 kBq/ml to 10.5 kBq/ml with a variability of 3%.

A method of verifying the calibration of PET scanners according to the present invention will now be described with reference to FIG. 4.

Subsequently, the applicant initially verified that a PET scanner is calibrated if the SUV measured by it (using a phantom of the type described above and a clock and an object of known weight as indicated above) has an associated error less than or equal to a predetermined percentage, in particular 3%.

The applicant then devised the following formula for calculating the propagation of the error in the SUV (to be used for the analyses conducted on the patients):

$$(\sigma_{SUV})^2 = \left(\frac{\delta_{SUV}}{\delta_{bodyweight}}\sigma_{bodyweight}\right)^2 + \left(\frac{\delta_{SUV}}{\delta_{[A_{PET}]}}\sigma_{[A_{PET}]}\right)^2 + \left(\frac{\delta_{SUV}}{\delta_{A_{inj}}}\sigma_{A_{inj}}\right)^2 + \left(\frac{\delta_{SUV}}{\delta_{A_{res}}}\sigma_{A_{res}}\right)^2 + \left(\frac{\delta_{SUV}}{\delta_{tupt}}\sigma_{tupt}\right)^2 + \left(\frac{\delta_{SUV}}{\delta_{tres}}\sigma_{tres}\right)^2 \quad (2)$$

where the subscripts are the same as those used previously in formula (1).

Finally, the applicant experimentally determined the values of the error percentages, shown below, which are to be associated with the various terms of equation (2) in such a way that the total percentage error in the determination of the SUV is less than the predetermined percentage indicated above.

The error percentages of the terms of equation (2) are preferably:

$\sigma_{APET}=3\%$;

$\sigma_{Ainj}=3\%$;

$\sigma_{Ares}=3\%$ $\sigma_{tupt}, \sigma_{tres} \leq 10$ s $\sigma_{bodyweight}=\pm 0.2$ kg The method of verifying the calibration of PET scanners according to the present invention comprises a first step 100 of positioning the phantom described above in a PET scanner to be calibrated.

The phantom is aligned, in a known way, so that the plane passing through the centres of the spheres 12 is coplanar with the central portion of the scanner in the axial direction and the first transverse axis 6a and the second transverse axis 6b correspond to the internal reference system of the scanner on the transaxial plane, within a predetermined distance, of 3 mm for example.

Alternatively, the centering can be carried out in a known way, if the PET scanner has calibrated lasers, by using lines present on the phantom which reproduce, respectively, the first, second and third transverse axis 6a, 6b and 18.

Subsequently, in step 102, the raw data are then acquired in the form of sinograms by carrying out a known PET/CT examination of the phantom. The acquisition is repeated three times with three different acquisition times, preferably 1×(mFD), 1.5×(mFD) and 5×(mFD), where mFD is the minimum frame duration.

The minimum frame duration (mFD) is calculated as follows:

$$t_{mFD} = \frac{5.3}{A_{phantom}} t_{std} \quad (3)$$

where $t_{std}$ is equivalent to 2 minutes for PET scanners with 3D acquisition and 3 minutes for PET scanners with 3D acquisition, and $A_{phantom}$ is the activity concentration in the phantom at the moment of acquisition of the PET images of the phantom.

At this point, in step 104, the sinograms obtained from the scanning of the phantom are reconstructed, using vendor-dependent iterative algorithms of a known type, and applying to the acquired data all the available corrections, including the attenuation correction based on CT.

The sinograms must be reconstructed by using the standard parameters recommended by the manufacturers of PET/CT scanners for forming PET images.

In step 106, the PET images are processed in a known way, by finding the values of some of the parameters to be used (for example $A_{PET}$), according to equation (1), to calculate the SUV of the phantom ($SUV_{phantom}$). The values of the other missing parameters for completing the calculation of equation (1), for example the weight of the phantom, $A_{inj}$, $A_{res}$, etc., are known in advance as a result of the construction of the phantom.

The SUV is calculated for a circular region of interest (ROI) having a predetermined diameter, for example 37 mm, located in the area surrounding the spheres 12 at a predetermined distance, for example 1.5 cm, from all the spheres 12 and from the wall of the phantom.

The SUV of the phantom ($SUV_{phantom}$) is then associated with an error of the phantom ($\sigma_{SUVphant}$) calculated according to the following formula:

$$(\sigma_{SUV_{phant}})^2 = \left(\frac{\delta SUV}{\delta_{weightphant}} \sigma_{weightphant}\right)^2 + \left(\frac{\delta SUV}{\delta_{[A_{PET}]}} \sigma_{[A_{PET}]}\right)^2 + \left(\frac{\delta SUV}{\delta_{A_{phantom}}} \sigma_{A_{phantom}}\right)^2 \quad (4)$$

where $A_{PET}$ is the concentration of radioactivity in the phantom at the time t of acquisition of the PET images (expressed in MBq/Kg);

$A_{phantom}$ is the total activity (expressed in MBq) in the phantom;

weightphant is the weight of the phantom expressed in kg.

Formula (4) is a simplification of formula (2), in which the last three addends of formula (2) are not used in formula (4) because no radiopharmaceutical is injected into the phantom and its activity is known in advance.

A specific correction factor for the scanner is then calculated, using the following formula:

$$CF_{scanner} = \left(\frac{SUV_{phantom}}{SUV_{theoretical}}\right) \quad (5)$$

where $SUV_{phantom}$ is the SUV calculated as described above in step 106 and $SUV_{theoretical}$ is the SUV calculated theoretically from the known activity of the matrices of germanium-68 and from the known weight of the phantom.

Finally, a check is made as to whether this value $CF_{scanner}$ lies within a predetermined range around the value $$1 \pm \frac{\sigma SUV_{phant}}{SUV_{theoretical}}.$$

If this condition is true, all the images obtained from the PET scanner will be used without applying any correction factor.

If this condition is false, all the images obtained from the PET scanner will be used with the application of the correction factor $CF_{scanner}$.

If the value of $SUV_{phantom}$ lies within a predetermined range, for example between 0.97 and 1.03 (a range of 3% around the value 1), the PET scanner is considered to be calibrated.

At this point the method of verifying the calibration of the PET scanner has been completed, and said scanner can be used to carry out PET analyses of patients.

The objective of the PET analyses of patients, as stated above, is the calculation of the SUV according to equation (1). In order to perform this calculation, the personal weighing scale must be calibrated, as described above, after the list of figures, and a calibrated clock must also be available.

The remaining task is to verify the calibration of the activity calibrator to be used, as this is required to calculate some of the parameters to be used in equation (1).

For this purpose, the reference sphere 13 is taken out of the phantom and is measured with the activity calibrator in order to verify the calibration of this calibrator. In fact, the activity concentration range $A_{reference\_sphere}$ of the reference sphere 13 is known in advance (since the reference sphere 13 has been filled with a solid matrix of germanium-68 as mentioned above), and furthermore the actual concentration of the reference sphere 13 is certified by a specialized authority.

Thus the calibrator can be used to measure the quantities found in formula (1), since it is certain that the values supplied and used for the calculation of the SUV will be consistent with the phantom parameters used to verify the PET scanner.

Naturally, the principle of the invention remaining the same, the forms of embodiment and details of construction may be varied widely with respect to those described and illustrated, which have been given purely by way of non-limiting example, without thereby departing from the scope of protection of the present invention as defined by the attached claims.

The invention claimed is:

1. Method for verifying the calibration of a PET scanner, comprising the steps of:
   positioning a phantom in the PET scanner, wherein the phantom comprises:
   a substantially cylindrical body having a cross section with a convex curvilinear profile;
   a plurality of spheres placed within the body, comprising a solid matrix of germanium-68; and
   a reference sphere filled with a solid matrix of germanium-68, the reference sphere being connected to the body in such a way that it can be removed and replaced in the same position;
   acquiring sinograms by performing a PET/CT examination of the phantom by means of the PET scanner;
   reconstructing the sinograms derived from the scanning of the phantom, producing PET images;
   processing said PET images in order to calculate a Standardized Uptake Value of the phantom ($Suv_{phantom}$);
   calculating the error ($\sigma_{SUVphant}$) of the Standardized Uptake Value of the phantom ($Suv_{phantom}$) according to the following formula:

$$(\sigma_{SUV_{phant}})^2 = \left(\frac{\delta_{SUV}}{\delta_{weightphant}}\sigma_{weightphant}\right)^2 + \left(\frac{\delta_{SUV}}{\delta_{[A_{PET}]}}\sigma_{[A_{PET}]}\right)^2 + \left(\frac{\delta_{SUV}}{\delta_{A_{phantom}}}\sigma_{A_{phantom}}\right)^2 \quad (4)$$

where $A_{PET}$ is the concentration of radioactivity in the phantom at the time t of acquisition of the PET images (expressed in MBq/Kg);
$A_{phantom}$ is the total activity (expressed in MBq) in the phantom;
weightphant is the weight of the phantom expressed in kg;
   calculating a specific correction factor for the scanner ($CF_{scanner}$) according to the formula: $CF_{scanner} = SUV_{phantom}/SUV_{theoretical}$ where $SUV_{theoretical}$ is the SUV calculated from the known activity of matrices of germanium-68 and from the known weight of the phantom; and
   verifying that said Standardized Uptake Value ($SUV_{phantom}$), corrected on the basis of the previously calculated $CF_{scanner}$, is within a predetermined range around the value 1.

2. Method according to claim 1, wherein in the phantom:
   the spheres are placed along an internal circumference having a predetermined diameter;
   the spheres are placed in a transverse way within the body so that the centres of the spheres are aligned along a transverse axis of the body;
   the phantom having a centre and a mounting plate, so that the centres of the spheres are placed at respective predetermined distances from the centre and mounting plate.

3. Method according to claim 1, wherein in the phantom the spheres and the reference sphere are filled with a solid matrix of germanium-68 having an activity concentration ($A_{spheres}$) four times greater than the area of the body surrounding the spheres.

4. Method according to claim 1, wherein in the phantom the number of spheres is five.

5. Method according to claim 4, wherein in the phantom the spheres have respective inside diameters of 10 mm, 13 mm, 17 mm, 28 mm and 37 mm.

6. Method according to claim 1, wherein in the phantom the spheres are made of polymethyl methacrylate or glass or other plastic material.

7. Method according to claim 1, wherein in the phantom the spheres are formed by a solid matrix of germanium.

8. Method according to claim 1, wherein in the phantom the reference sphere has a diameter of 22 mm.

9. Method according to claim 3, wherein in the phantom the spheres and the reference sphere are filled with a solid matrix of germanium-68 having an activity concentration ($A_{spheres}$) in the range from 42.4-10.6 kBq/ml.

10. Method according to claim 1, wherein the Standardized Uptake Value is calculated for a circular region of interest (ROI) having a predetermined diameter, located in the area surrounding the spheres at a predetermined distance from all the spheres and from the wall of the phantom.

11. Method according to claim 1, comprising using a kit comprising the phantom, a calibrated clock and one or more objects of predetermined weight.

12. Method according to claim 2, wherein in the phantom the spheres and the reference sphere are filled with a solid matrix of germanium-68 having an activity concentration ($A_{spheres}$) four times greater than the area of the body surrounding the spheres.

13. Method according to claim 2, wherein in the phantom the number of spheres is five.

14. Method according to claim 13, wherein in the phantom the spheres have respective inside diameters of 10 mm, 13 mm, 17 mm, 28 mm and 37 mm.

15. Method according to claim 2, wherein in the phantom the spheres are made of polymethyl methacrylate or glass or other plastic material.

16. Method according to claim 2, wherein in the phantom the spheres are formed by a solid matrix of germanium.

17. Method according to claim 12, wherein in the phantom the spheres and the reference sphere are filled with a solid matrix of germanium-68 having an activity concentration ($A_{spheres}$) in the range from 42.4-10.6 kBq/ml.

18. Method according to claim 2, comprising using a kit, comprising the phantom, a calibrated clock and one or more objects of predetermined weight.

19. Method according to claim 4, wherein in the phantom the reference sphere has a diameter of 22 mm.

\* \* \* \* \*